(12) United States Patent
Dafni et al.

(10) Patent No.: US 8,831,319 B2
(45) Date of Patent: Sep. 9, 2014

(54) METHOD AND SYSTEM FOR CALIBRATING CT IMAGES

(75) Inventors: Ehud Dafni, Caesarea (IL); David Ruimi, Ganot Hadar (IL)

(73) Assignee: Arineta Ltd., Caesarea (IL)

( * ) Notice: Subject to any disclaimer, the term of this patent is extended or adjusted under 35 U.S.C. 154(b) by 696 days.

(21) Appl. No.: 12/946,885

(22) Filed: Nov. 16, 2010

(65) Prior Publication Data

US 2011/0116697 A1 May 19, 2011

Related U.S. Application Data

(60) Provisional application No. 61/281,255, filed on Nov. 16, 2009.

(51) Int. Cl.
*G06K 9/00* (2006.01)
*G06T 11/00* (2006.01)

(52) U.S. Cl.
CPC ......... *G06T 11/008* (2013.01); *G06T 2211/432* (2013.01)
USPC .......................................................... 382/131

(58) Field of Classification Search
None
See application file for complete search history.

(56) References Cited

U.S. PATENT DOCUMENTS

| | | | |
|---|---|---|---|
| 4,646,334 A * | 2/1987 | Zerhouni | 378/18 |
| 4,724,110 A * | 2/1988 | Arnold | 264/102 |
| 5,008,822 A | 4/1991 | Brunnett et al. | |
| 5,068,788 A | 11/1991 | Goodenough et al. | |
| 6,990,222 B2 | 1/2006 | Arnold | |
| 7,388,973 B2 * | 6/2008 | Fidrich et al. | 382/128 |
| 8,186,880 B1 * | 5/2012 | Arnold | 378/207 |
| 2004/0102688 A1 * | 5/2004 | Walker et al. | 600/407 |
| 2009/0074278 A1 * | 3/2009 | Beaulieu et al. | 382/131 |

* cited by examiner

*Primary Examiner* — Nancy Bitar

(57) ABSTRACT

A method of correcting CT numbers in image data includes selecting at least one reference region in a CT image, wherein the selected region is a region associated with substantially same CT number when no artifacts are present in the CT image, estimating artifacts in at least one other region of the CT image based at least in part on detected CT numbers in the at least one reference region, and correcting CT numbers in the at least one other region of the CT image based on the estimated artifacts.

38 Claims, 8 Drawing Sheets

METHOD AND SYSTEM FOR CALIBRATING CT IMAGES

RELATED APPLICATION/S

This application claims the benefit of priority under 35 U.S.C. §119(e) of U.S. Provisional Patent Application No. 61/281,255 filed on Nov. 16, 2009, the contents of which are incorporated herein by reference in their entirety.

FIELD OF THE INVENTION

The present invention, in some embodiments thereof, relates to Computerized Tomography (CT) imaging and, more particularly, but not exclusively, to image processing of image data obtained by a CT scanner.

BACKGROUND OF THE INVENTION

Computerized Tomography (CT) scanners produce images of a subject by reconstruction of X-ray attenuation data acquired over multiple view angles. Typically, images are constructed by back projecting the view data received from the CT detector over the multiple views. CT images are representation of the X-ray attenuation coefficient at each image pixel, referred to as a CT number. The CT number typically provides information regarding density of the tissue. In medical imaging, a CT number −1000 is commonly associated with air (no attenuation) whereas CT number 0 is associated with water.

Analysis of image data can be qualitative or quantitative. In qualitative analysis, subjective viewing of images is used to identify boundaries of tissues, organs and foreign masses and/or to discriminate between tissue types based on differences in density across the image.

Quantitative analysis relies on the actual CT numbers of the image to provide information on actual densities and/or compositions of a Region Of Interest (ROI). Exemplary applications using qualitative analysis of CT images include Coronary Artery Calcium (CAC) testing to evaluate calcified plaque in the coronary arteries, bone mineral density evaluation, fat content of tissue evaluation, iron build up in liver evaluation, and contrast agent perfusion determination.

In order to perform quantitative analysis of true tissue densities, calibration of the CT numbers is performed to improve reliability of the CT numbers to be used to determine density.

Artifacts can be caused, for example, by beam hardening, thermal drifts in an acquisition system, inaccurate subtraction of a signal from scattered radiation, truncation as described herein below, and variability in tissue surrounding the field of view. Truncation artifacts typically occur when the scanned Field of View (FOV) is smaller than the patient size. Artifacts may impose a global shift in CT numbers such as global increase or global decrease of the CT number across the entire image or may impose spatial variations in CT numbers across an image so structures or tissues of uniform density display spatially varying CT numbers. In particular, artifacts known in the art as "cupping" involve CT number variation with radial symmetry relative to the image center.

CT scanners typically correct for spatial variations in CT number using a procedure known in the art as "phantom calibration." Objects of known material and density are scanned prior to patient scan and calibration tables are calculated and applied to patient scan data. In addition, some CT scanners apply empirical correction known in the art as polychromatic correction, wherein scan data is arbitrary modified according to a formula or look-up table. Such corrections reduce the artifact level but cannot fully correct for every patient and every cross section within the patient.

Some calibration processes correct for relative efficiency and gain of the detector array elements and variation in X ray beam intensity across the irradiation field. One example of such calibration is known in the art as "air calibration". Typically, air calibration involves performing a scan using a CT scanner, without there being a subject or phantom in the imaging space between the X ray source and the detector, so the detector array is irradiated by un-attenuated X ray beam. The acquired date, sometimes termed "air calibration data" is indicative of the relative efficiency and gain of the detector array elements and the variation in X ray beam intensity across the irradiation field. The air calibration data is used to normalize the attenuation data acquired during a subject scan.

U.S. Pat. No. 5,068,788 entitled "Quantitative computed tomography system," the contents of which is incorporated by reference, describes a method of analyzing a suitably chosen CT number histogram to reduce the effects of background scatter and intermixing of tissues. CT numbers of individual tissues are obtained by locating leading edges of histogram distribution curves in regions of the histogram representing the individual tissues. The leading edge values are used as a starting point for construction of model curves representative of pure tissue samples against which the actual histogram distribution can be measured, by calculating and adjusting moments of the curve, following subtraction of assumed values for background and intermixing derived from the leading edge values. The adjusted CT numbers are used to create a reference plot by which other CT numbers can be converted to a physical quantity such as density for use in analyzing other tissues.

U.S. Pat. No. 6,990,222 entitled "Calibration of tissue densities in computerized tomography," the contents of which is incorporated by reference, describes a hybrid calibration method that uses an calibration phantom (exterior reference) scanned simultaneously with a patient, and one or more known tissues of the subject (interior reference) to create a hybrid calibration reference that improves the measurement of tissue densities throughout the body. In addition, the calibration method is used to quantitatively define boundaries of tissue and organs for more accurate measurements of lengths, areas and volumes.

Some known image processing techniques for processing CT images involve forward projecting processed image data to reconstruct view data. After further processing, the forward projected data may be back projected to reconstruct the image data.

U.S. Pat. No. 5,008,822, entitled "Combined high speed back projection and forward projection processor for CT systems," the contents of which is incorporated by reference, describes A CT scanner that generate views of data such as equal angular increment detector fan views which are convolved or filtered by an array processor. A combined back projector and forward projector back projects the data from the array processor into an output memory and forward projects lines of image representation data from an input memory to the output memory. Each view representation may again be an equal angular increment detector fan format view, a parallel ray format view, an equal linear increment source fan format view, a source fan format view, an equal angular incremental detector fan format, an equal linear increment detector fan format, or an equal angular increment source fan format.

SUMMARY OF THE INVENTION

According to an aspect of some embodiments of the present invention, there is provided a method and system for calibrating CT numbers in ROI of an object imaged based on CT numbers detected in other portions of that object in the same image. In some exemplary embodiments, the object is a patient. According to some embodiments of the present invention, the selected region is a region associated with a known CT number and correction and/or calibration is based on comparing the measured CT in the selected region to the known CT for that region.

According to an aspect of some embodiments of the present invention there is provided a method and system for calibrating CT numbers in a CT image to correct for artifacts that spatially vary the CT numbers across the CT image, e.g. 2-D and/or volumetric image. According to some embodiments of the present invention, calibration is based on identifying regions that are qualitatively determined to have common density even though their associated CT numbers vary over the CT image. According to some embodiments of the present invention, the CT numbers are corrected over a first correction step based on analysis of image data and then further processed based on forward projected view data of the corrected image.

According to an aspect of some embodiments of the present invention there is provided a method of correcting CT numbers in image data, the method comprising: selecting at least one reference region in a CT image, wherein the selected region is a region associated with substantially same CT number when no artifacts are present in the CT image; estimating artifacts in at least one other region of the CT image based at least in part on detected CT numbers in the at least one reference region; and correcting CT numbers in the at least one other region of the CT image based on the estimated artifacts.

Optionally, the selecting includes selecting a plurality of reference regions dispersed across the CT image.

Optionally, the method further includes segmenting of image parts including the substantially same CT number.

Optionally, the at least one reference region is a region associated with a pre-known CT number.

Optionally, the method further includes calibrating the CT numbers based on a difference between the pre-known CT number and an average CT number in the at least one reference region.

Optionally, the at least one reference region is a region of muscle tissue, fat, blood, or brain tissue.

Optionally, selecting the at least one reference region is performed by computer assisted selection.

Optionally, the CT number is determined from an average of pixel values over a defined area in the CT image Optionally, the method includes defining a surface shape function of the at least one other region from detected CT numbers in the at least one reference region.

Optionally, estimating artifacts in the at least one other region of the CT image is based on interpolation of CT number gradients determined from the at least one reference region.

Optionally, selecting at least two reference regions, wherein the CT image includes a stack of images and wherein selecting at least two reference regions includes selecting reference regions from different images in the stack.

Optionally, the CT image is one of a stack of images, and wherein the correcting is performed on the stack of images based estimating artifacts on one or more images of the stack.

Optionally, the CT image includes a volumetric image and wherein selecting at least two reference regions includes selecting volumetric regions.

Optionally, the method includes assessing the flatness of the CT image based on detected CT numbers in the at least one reference region.

Optionally, the method includes selecting at least two reference regions associated with a different pre-known CT number.

Optionally, the at least one other region is a region of interest from which a quantitative analysis is performed.

Optionally, the method includes forward projecting the calibrated image data; processing the forward projected data; and back projecting the forward projected data.

According to an aspect of some embodiments of the present invention there is provided a scanning system providing corrected CT image data comprising: a data acquisition unit for acquiring view data from a detector in a CT scanner; an image reconstruction unit for reconstructing image data from the view data; and an image processing unit for calibrating image data reconstructed from the image reconstruction unit, wherein the image processing unit is operative to analyze CT numbers in at least one selected reference region and to estimate artifacts in at least one other region of the CT image at least partially based on analysis of the CT numbers in the at least one selected reference region, wherein the at least one selected reference region is a region associated with a substantially same CT number when no artifacts are present in the CT image.

Optionally, the image processing unit is operative to select the reference regions.

Optionally, the image processing unit is operative to select regions associated with pre-known CT numbers.

Optionally, the image processing unit is operative to select regions of at least one of muscle tissue, fat, blood, and brain tissue.

Optionally, the image processing unit is operative to segment image parts known to include a substantially same CT number.

Optionally, the image processing unit is operative to define a shape function for the at least one other region of the CT image based on detected CT numbers in the at least one reference region.

Optionally, the image processing unit is operative to estimate artifacts in the at least one other region of the CT image based on interpolation of CT number gradients determined from the at least one reference region.

Optionally, the CT image is a volumetric image and wherein the image processing unit is operative to select at least one reference region includes selecting a volumetric reference region.

Optionally, the CT image is one of a stack of CT images, and wherein the image processing unit calibrates the stack of images based estimating artifacts on one or more images of the stack.

Optionally, the image processing unit is operative to assess a flatness of the CT image based on detected CT numbers in the at least one reference region.

Optionally, the image processing unit is operative to perform quantitative analysis on the at least one other region, wherein the quantitative analysis includes one of coronary artery calcium testing, bone mineral density evaluation, fat content of tissue evaluation, iron build up in liver evaluation, and contrast agent perfusion determination.

Optionally, the image processing unit is operative to forward projecting calibrated image data, processing the forward projected data.

According to an aspect of some embodiments of the present invention there is provided a method of correcting CT numbers in image data, the method comprising: selecting at least one reference region in a CT image of a patient, wherein the selected region is a region with a known CT number; estimating artifacts in at least one other region of the CT image of the patient based on comparing detected CT numbers in the at least one reference region and known CT numbers for that region; and correcting CT numbers in the at least one other region of the CT image based on the estimated artifacts.

Optionally, the detected CT numbers are average CT numbers over a sample area of the reference region.

Optionally, the at least two reference regions are regions of muscle tissue, fat, blood, or brain tissue of the patient.

Optionally, the CT image is one of a stack of images, and wherein the correction is performed on the stack of images based estimating artifacts on one or more images of the stack.

Optionally, the CT image includes a volumetric image and wherein selecting at least one reference region includes selecting a volumetric region.

Optionally, the at least one reference region includes at least two regions associated with a different pre-known CT number.

Optionally, the at least one other region is a region of interest from which a quantitative analysis is performed.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings and images. With specific reference now to the drawings and images in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
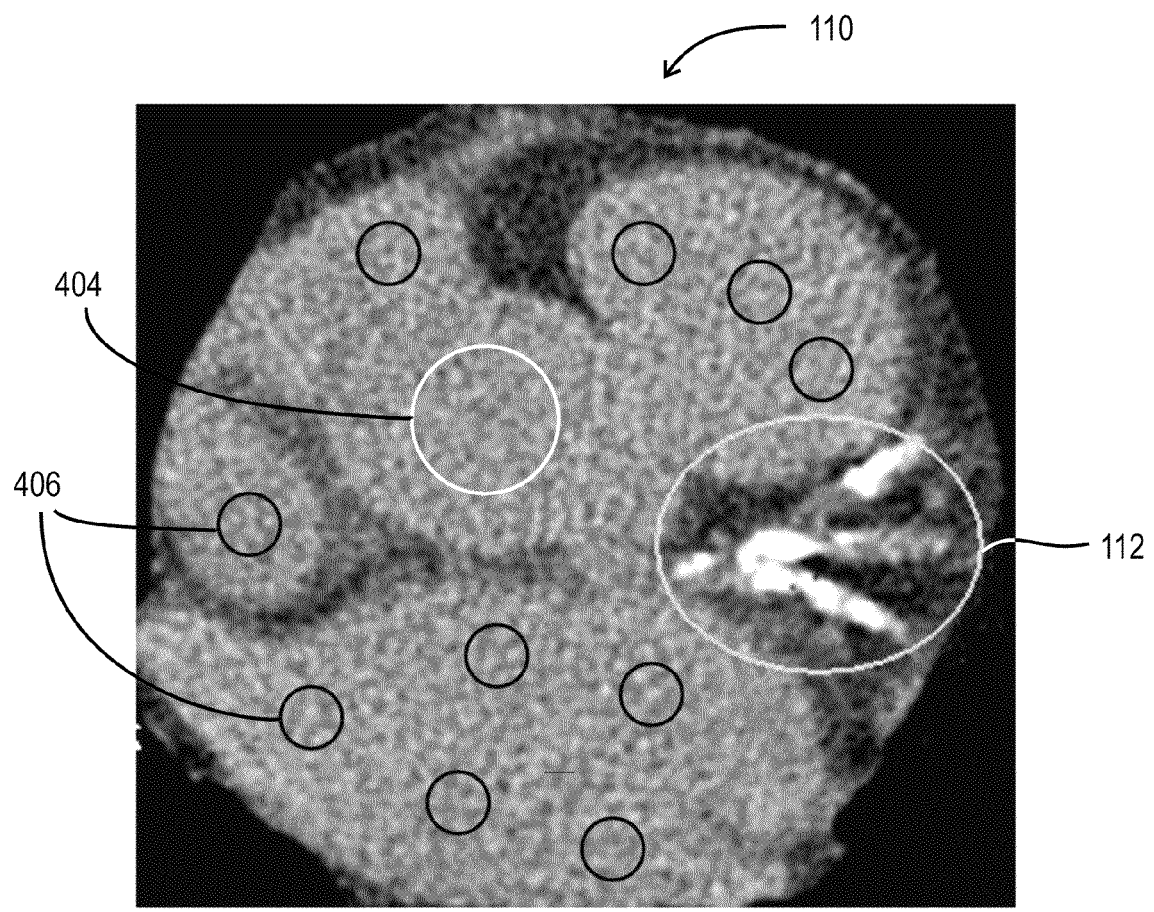
FIG. 1 is an exemplary CT image of an axial slice of a heart including a ROI and reference regions that are marked in accordance with some embodiments of the present invention.

The present invention, in some embodiments thereof, relates to Computerized Tomography (CT) imaging and, more particularly, but not exclusively, to image processing of image data obtained by a CT scanner.

As used herein the term/phrase "flat image" means an image where structures or tissues of uniform density are represented by a substantially same CT number in all regions of the image and the term "non-flat image" means an image where structures or tissues of uniform density are represented by a plurality of different CT number across the image. The terms "same CT number" and "different CT number" herein refer to CT number variation larger than the variation due to statistical noise in the image. The term "artifacts" refers to phenomena resulting in erroneous CT numbers in images. Substantially same CT number means CT numbers within image statistical noise range and natural variation of CT number range in image parts corresponding to a uniform organ tissue or uniform material. In some exemplary embodiments, a substantially same CT number is in the range of +/−3 CT numbers. Optionally for some organs, e.g. muscle and fat, and/or for higher noise images the range is larger. Optionally a substantially same CT number is in the range of +/−5 CT numbers or +/−10 CT numbers or +/−20 CT numbers.

An aspect of some embodiments of the present invention provides for correcting and/or calibrating CT numbers in at least one region in a CT image (ROI) based on measured CT numbers in a selected other region(s) (reference region) of the CT image where both the ROI and reference region are from the object being examined. In some exemplary embodiments, the object being examined is a patient. The ROI and/or the reference regions may be selected from a single CT image, e.g. image slice, a stack of images and/or a volumetric image. According to some embodiments of the present invention, the selected region is a region associated with a known CT number and correction and/or calibration is based on comparing the measured (and/or detected) CT in the selected region to the known CT for that region. In some exemplary embodiments, a plurality of regions is selected. Optionally, all the selected regions are known to have the same known CT number. Typically a shift in CT numbers is defined for the entire image based on the difference determined between the measured CT in the selected region(s) to the known CT for that region. Typically, the regions selected are regions known to have relatively uniform density for most people such as muscle tissue, fat, blood, and brain tissue and for which CT numbers can be predicted.

An aspect of some embodiments of the present invention provides for assessing flatness of CT image data from measured CT numbers in one or more selected regions in an image and correcting CT numbers in a ROI based on the assessed data. According to some embodiments of the present invention, image flatness is assessed by analysis of CT numbers in selected regions in an image. Flatness may be assessed in a single CT image, a stack of CT images and/or in a volumetric CT image. Typically, the selected regions are regions other than the ROI. According to some embodiments of the present invention, the selected regions are regions with pre-known density (and pre-known associated CT numbers). Typically, the regions selected are regions known to have relatively uniform density for most people such as muscle tissue, fat, blood, and brain tissue and for which CT numbers can be predicted. Optionally, the selected region is a region of a phantom imaged together with the patient or other examine object. Alternatively, the selected regions are regions that can be qualitatively determined to have a common density even if the actual density value is not known. Selected regions may be manually identified by a user viewing the CT image and marking the identified regions, semi-automatically by computer assisted identification of the regions and/or automatically by image processing techniques. Optionally, the regions selected are regions that are dispersed across the image. Optionally, regions having different pre-known densities are selected.

According to some embodiments of the present invention, CT numbers in selected regions are compared to evaluate image flatness, e.g. determine if the image is a flat image or a non-flat image. Variations and/or gradients in the CT numbers across the identified regions identified as having a common density are used as indication that the image is non-flat. Optionally, average CT numbers over defined sample areas are used to identify variations and/or gradients in CT numbers due to artifacts. Typically, variations and/or gradients above a defined threshold indicate a non-flat image. In some exemplary embodiments, an origin of the artifact, e.g. truncation and cupping and/or features of the artifact, e.g. symmetrical features are identified based on the analysis of the CT numbers over the identified regions.

According to some embodiments of the present invention, if the image is determined to be non-flat, the variations and/or gradients of the CT numbers in the selected regions are mapped and used to model the artifacts in other areas of the image. According to some embodiments of the present invention, a surface function across the image is defined based on measured CT numbers in the selected regions. Optionally, the surface function is tailored to specific type of artifact such as cupping artifacts that are typically have radial symmetry about the image center and/or artifacts that are either symmetrical or asymmetrically. Optionally, different surface functions are defined over different portions of the image. Optionally, a local surface function is defined based on CT numbers in selected reference regions that surround a ROI. In some exemplary embodiments, interpolation and/or extrapolation of gradients are used to predict and/or estimate gradients in areas outside the identified regions.

In some exemplary embodiments, the image is further calibrated based on the known densities of one or more identified region and/or based on a phantom scanned together with a scanned subject.

According to some embodiments of the present invention, after a flatness correction (and possibly other corrections), the image is forward projected to reconstruct view data. Optionally, forward projected view data is then compared to, e.g. subtracted from back projected view data, so that correction data to flatten the image can be further processed, e.g. smoothed. Typically, once processed, the subtracted data is reintroduced to previous view data, e.g. back projected view data and the image is the image is reconstructed. Optionally this process is iteratively repeated until differences between a previous view data and the back projected view data are small.

According to some embodiments of the present invention, calibration is applied on single image slice, on a stack of images or on a volumetric image. Optionally, a region in one image or layer in a volume is used to correct data in at least one other image or layer in the volume.

According to some embodiments of the present inventions, the calibration methods described herein are applied to correct for truncated view data or cupping. Optionally, calibration methods described herein can be used in CAC scoring, bone mineral density evaluation, fat content of tissue evaluation, iron build up in liver evaluation, and/or contrast agent perfusion determination An aspect of some embodiments of the present invention provides for a CT scanner including an associated image processing unit that is adapted to model spatial variations in CT numbers due to artifacts based on image data obtained from regions in a CT image with known densities. Optionally, modeling is performed on a stack of CT images and/or a volumetric CT image. According to some embodiments of the present invention, the image processing unit is further adapted to calibrate the CT numbers based on the model.

According to some embodiments of the present invention, the CT scanner is adapted to assess flatness of an image automatically without user intervention and/or semi-automatically based on input by a user. In some exemplary embodiments, the CT scanner is adapted to identify regions in a CT image with known density based on qualitative analysis of the image. In some exemplary embodiments, the scanner is adapted to assist a user to identify regions in a CT image with known density in a semi-automatic procedure. Optionally, the image processing unit is operable to iteratively reconstruct scan data.

Reference is now made to FIG. 1 showing an exemplary CT image of an axial slice of a heart including a ROI and reference regions that are marked in accordance with some embodiments of the present invention. Image 110 is an exemplary axial slice through the heart including ROI 112 showing calcified sections of coronary arteries that may be used in a CAC test. Typically, CT numbers identified as calcified plaque in the coronary arteries are processed to calculate a quantitative score. Accurate calculation of the CAC score depends on accurate measurement of the CT numbers of the calcified plaque. Any global and/or spatial varying artifacts in ROI 112 may compromise the accuracy of the CAC test.

The present inventors have found that CT images, e.g. image 110 typically include one or plurality of regions with known density (and known associated CT number) outside a ROI that can be used to estimate and/or predict both global and spatially varying artifacts. According to some embodiments of the present invention, regions with pre-known densities are identified based on qualitative examination of image 110 and used as reference regions to calibrate measured CT numbers in ROI 112. Qualitative analysis and/or identification may be performed manually as an operator views the displayed image, semi-automatically with computer assisted detection and/or automatically by the CT system based on parameters for detection stored in memory.

For example, in image 110, regions 404 and 406 have been identified as reference regions with pre-known density. Reference region 404 is marked over the ascending aorta filled with blood and reference regions 406 are marked over muscle tissues and/or volume filled with blood. Density and associated CT number for flowing blood is known and is typically practically invariant between people. Typically flowing blood (without addition of contrast agent) and muscle tissue have substantially the same CT number within accuracy sufficient for many applications. Other reference tissues that can be used in other body parts include, for examples, white brain matter, fat, e.g. fat in areas where it is not mixed with other tissues, muscles, and liver. In some exemplary embodiments, CT numbers measured in regions 404 and 406 are compared with known CT numbers associated with flowing blood and muscle tissue and the determined discrepancies between measured CT numbers and known CT numbers associated with such tissue is used to predict and/or estimate artifacts and CT number inaccuracies in image 110 in general and in ROI 112 in particular. According to some embodiments of the present invention, regions 406 and 404 are defined as sample area regions and an average CT number of each region is used to compare with known CT numbers. Optionally, a soft reconstruction filter is applied during image reconstruction and/or image smoothing is applied as known in art to reduce noise and regions 406 and 404 are defined based on smoothed CT numbers.

Figure 2:
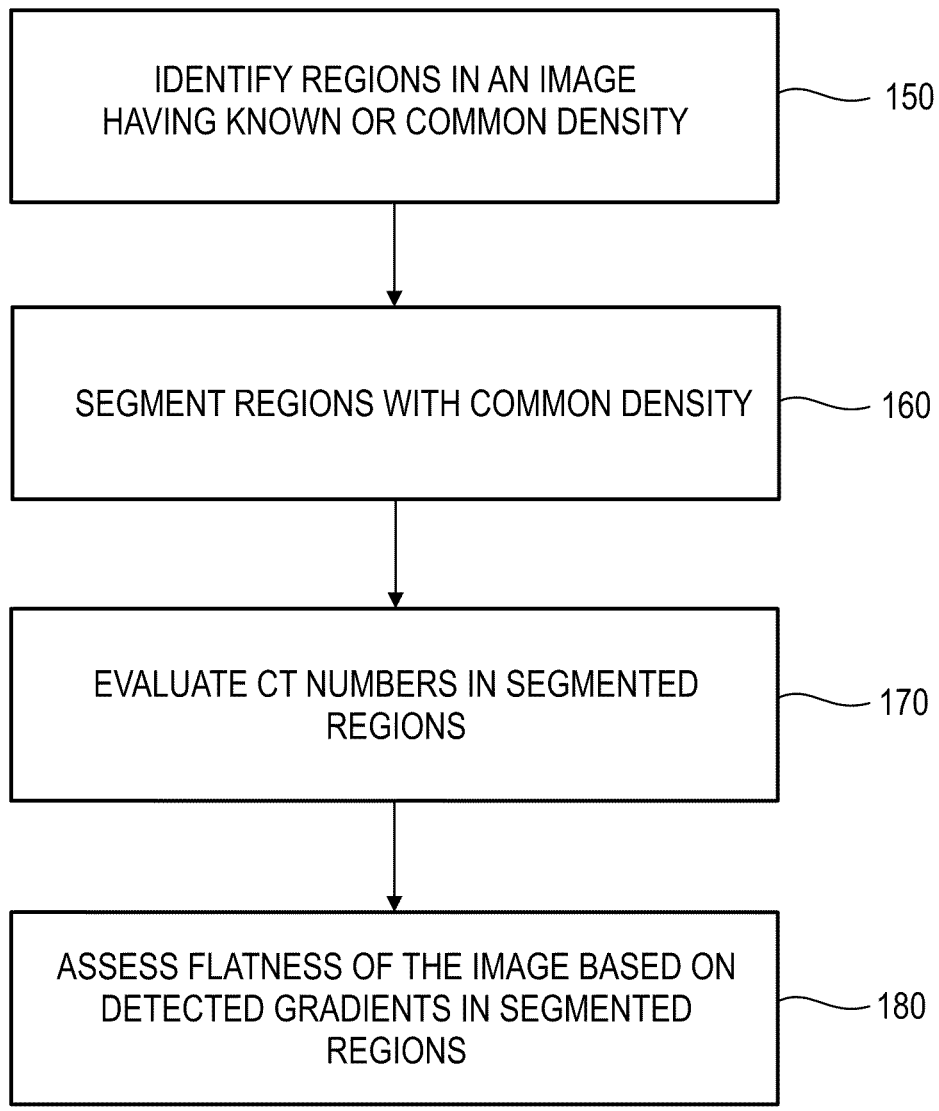
FIG. 2 is a simplified flow chart of an exemplary method for assessing flatness of an image in accordance with some embodiments of the present invention.

Reference is now made to FIG. 2 showing a simplified flow chart of an exemplary method for assessing flatness of an image in accordance with some embodiments of the present invention. According to some embodiments of the present invention, an image or images are qualitatively analyzed to identify regions with pre-known densities and/or pre-known CT numbers (block 150). Reference regions may be identified in a single image slice, e.g. image 110, a stack of images and/or a volumetric image. In some exemplary embodiments, identification of reference regions is performed manually by an operator and marking areas in the images is performed by placing graphical markings on a computer displayed image. In some exemplary embodiments, for volumetric images, the identified region is a volumetric region. Typically, a plurality of reference regions is selected across different parts of the image. Optionally, reference regions are areas expected to represent same CT number on different parts of the image, even if the CT number is not pre-known. In some exemplary embodiments, reference regions are suggested by computer selection and edited by a user.

According to some embodiments of the present invention, the image is segmented to outline sub-structures or tissues with known common density (block 160) based on identified reference regions. Typically, segmentation provides for increasing an area on the image that can be used as a reference region. Algorithms and methods for image segmentation are known and software packages are available for this task. Such algorithms may comprise one or several of edge detection, region growing, histogram analysis and other algorithms.

Figure 3:
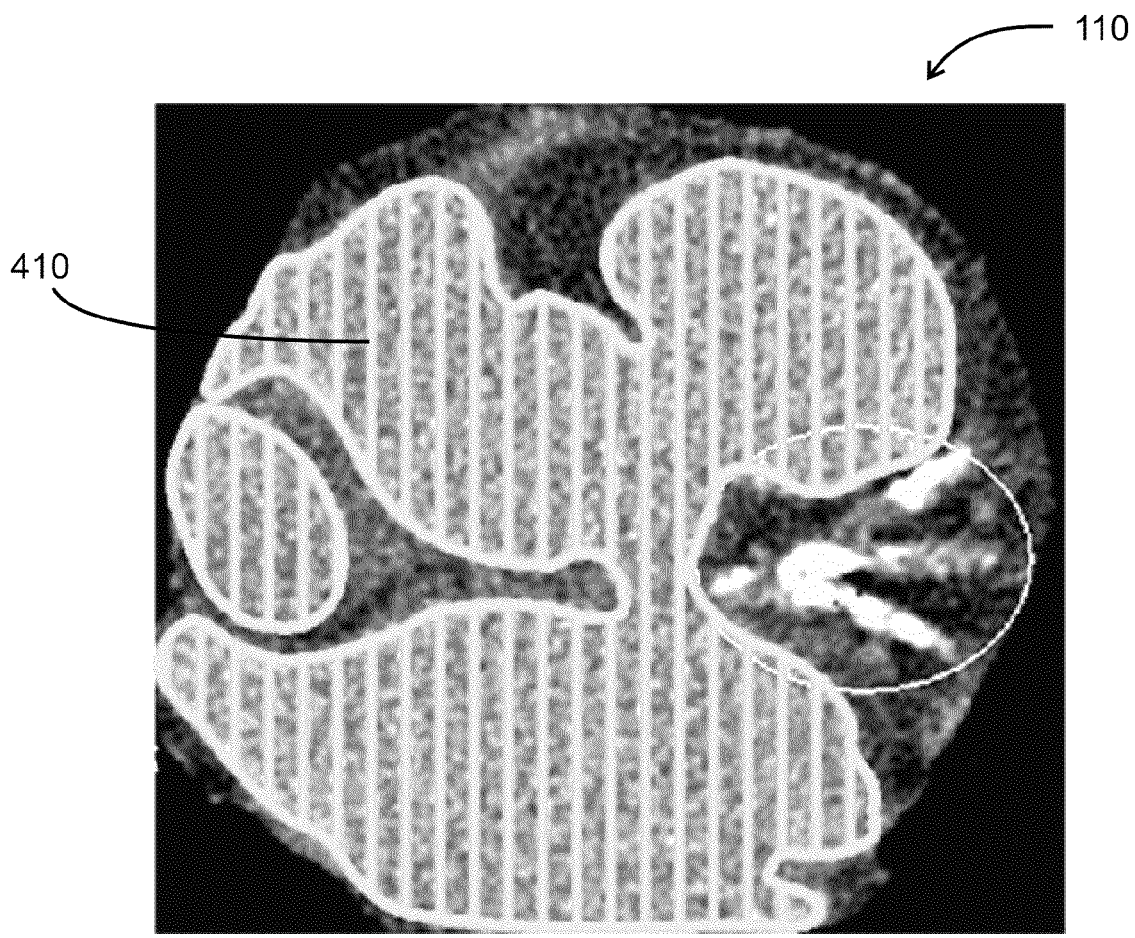
FIG. 3 is an exemplary CT image of axial slice of a heart from which a reference tissue has been segmented and marked in accordance with some embodiments of the present invention.

Reference is now made to FIG. 3 showing an exemplary CT image of axial slice of a heart from which a reference tissue has been qualitatively segmented and marked in accordance with some embodiments of the present invention. In some exemplary embodiments, when the image is qualitatively determined to be relatively flat, a segmentation algorithm may be defined to rely on CT numbers uniformity within defined noise limits for segmentation. In other exemplary embodiments, for non-flat images, a segmentation algorithm is defined to allow for slow and/or steady variation in the average CT numbers in defined sample areas across the segmented tissue.

Segmentation of reference areas may be done manually, semi automatically or fully automatically. In some exemplary embodiments, during manual segmentation, a user may draw a contour around boundaries of reference tissue. In some exemplary embodiments, during semi automatic operation the user marks a seed or seeds on the reference tissue and the algorithm finds the contours at the tissue boundaries. Optionally, the user may then adjust the contours manually. According to some embodiments of the present invention, during automatic segmentation, an algorithm may use expected or known anatomy to segment a reference tissue. In some exemplary embodiments, when flatness is assessed over a stack of images or a volume, segmentation of one image may be used to guide the segmentation of the next image or next layer in the volume.

Referring back to FIG. 2, according to some embodiments of the present invention, measured CT numbers within the segmented regions are evaluated (block 170). Optionally, CT numbers in the segmented regions may be smoothed and evaluation may be performed on the smoothed data. In some exemplary embodiments, average CT numbers data and/or histograms are determined by the CT system and presented to an operator for evaluation. According to some embodiments of the present invention, flatness is assessed based on detected gradients in the segmented regions (block 180). Optionally, if all average CT numbers within the segmented reference regions (determined to have a common CT number) fall within a predetermined range the image is considered flat. Optionally, gradients identified in the CT numbers are used to assess that the image is not-flat. Assessment of image flatness can be taken for each image separately or can be made for a stack of images or a volumetric based one or more single images.

Optionally, flatness is further assessed based on analysis of raw view data to determine possible truncation of the data. Optionally, raw view data is further examined to determine if a patient's size exceeds a calibrated range of patient sizes. Optionally, images from oversized patients are assessed as non-flat images. In some exemplary embodiments, image flatness is assessed based on CT numbers in a ROI (as opposed to or in addition to the assessment made based on the reference regions). Optionally, if all CT numbers in a ROI fall between a predetermined range, the ROI is considered flat. In some exemplary embodiments, a range of ±4 CT is sufficient for flatness. Typically, the range is application specific.

Figure 4:
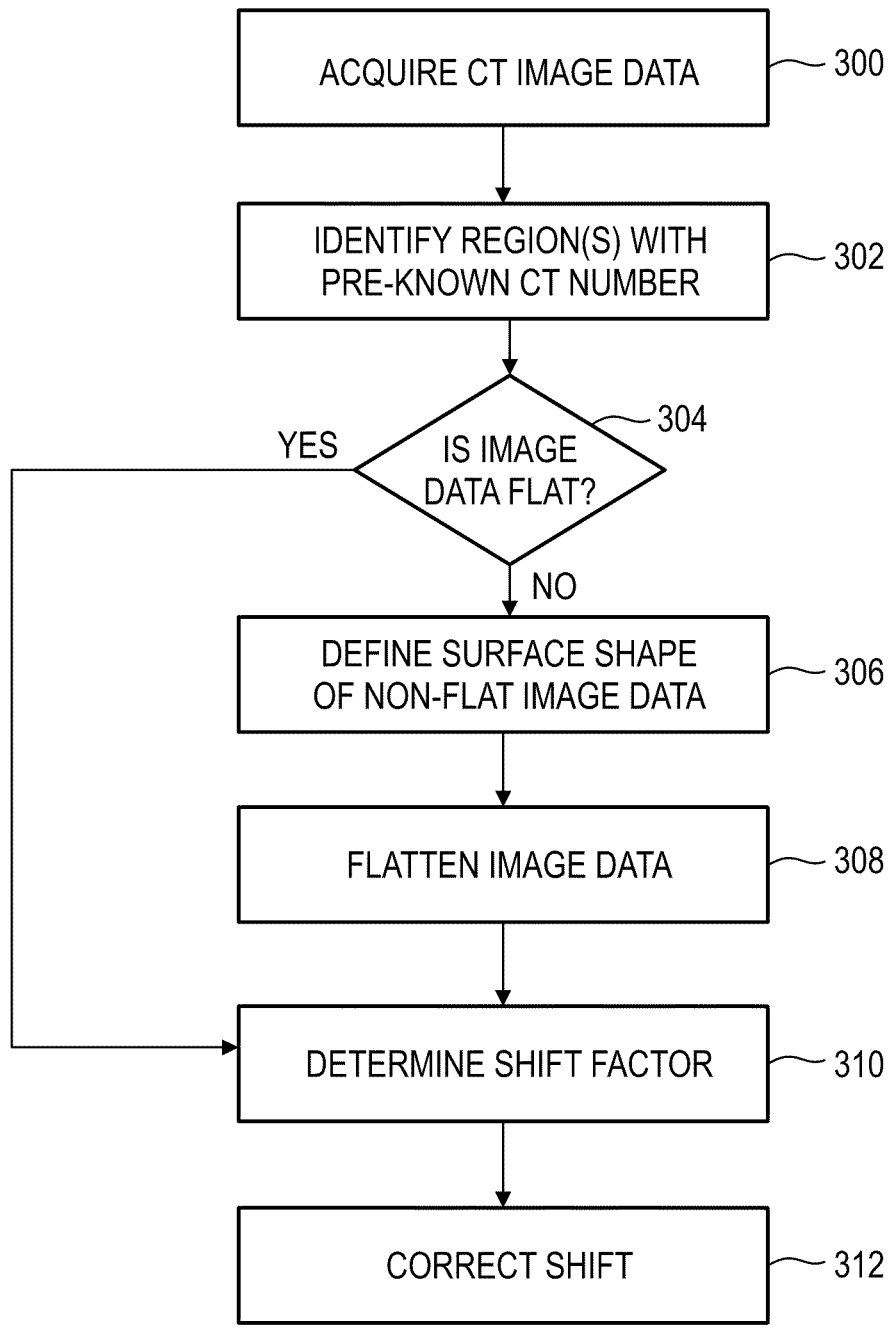
FIG. 4 is a simplified flow chart of an exemplary method for calibrating CT numbers using a surface function defined from CT numbers in a reference region(s) in accordance with some embodiments of the present invention.

Reference is now made to FIG. 4 showing a simplified flow chart of an exemplary method for calibrating an image based on a surface function defined for the image in accordance with some embodiments of the present invention. According to some embodiments of the present invention, CT image data is acquired (block 300) and regions with pre-known CT numbers are identified (block 302) as described for example in reference to FIGS. 1-3. As described above, image data includes single slice images, a stack of images and/or a volumetric image. According to some embodiments of the present invention, flatness of the image data is assessed based on measured CT numbers in the identified regions (block 304). Optionally, flatness is assessed based on additional information and/or other information for example as described in reference to FIG. 2. Typically, different applications require different levels of accuracy and image flatness is defined based on the requirements of the application. Typically, if an image is determined to be non-flat, e.g. not sufficiently flat a correction is imposed to flatten the image.

According to some embodiments of the present invention, if image data is determined to be non-flat, a surface shape of the image data is defined (block 306) so that a shape of the spatially varying artifact can be predicted. In some embodiments, CT numbers from reference regions, e.g. segmented reference regions, is fit to a surface function SF(x,y) of the form of second order polynomial, such as:

$$SF(x,y)=a_{00}+a_{10}x+a_{01}y+a_{11}xy+a_{20}x^2+a_{21}x^2y+a_{02}y^2+a_{12}xy^2+a_{22}x^2y^2 \quad \text{(Equation 1)}$$

Where (x,y) are the coordinates of the image pixels relative a center of rotation of the scanner and $a_{ij}$ are fit coefficients. Optionally, this fit can be accomplished, for example, by computer program Polyfitn by John D'Errico, available via Mathworks.com file exchange server, or by other computer programs and known algorithms. It is noted, that although SF(x,y) may be defined about the center of rotation, SF(x,y) may not necessarily have radial symmetry. Optionally, asymmetry is expected, e.g. wherein the scanned subject is positioned off the center, Equation 1 is applied for $(x-x_o)$ and $(y-y_o)$ where $x_o$ and $y_o$ are offset parameters.

In some exemplary embodiments, if the spatially variant artifact is suspected (or qualitatively determined) to have radial symmetry (cupping), a function of the form of Equation 2 is used:

$$SF(x,y) = a_{00} + a_1 r + a_2 r^2 \quad \text{(Equation 2)}$$

Where r is the distance of a pixel from the center of rotation.

It is appreciated that the surface functions defined in Equation 1 and Equation 2 are exemplary and optionally higher order polynomials or other functions may be used to define surface shape of non-flat image data.

According to some embodiments of the present invention, image data is flattened based on the defined surface shape of the non-flat image data (block 308) and corrected CT numbers ($CT_{corr}$) are obtained with Equation 3:

$$CT_{corr}(x,y) = CT_{meas}(x,y) \times (1000 + CT_{ref})/(1000 + SF(x,y)) \quad \text{(Equation 3)}$$

Where $CT_{meas}(x,y)$ is the measured CT number at coordinate (x,y), SF(x,y) is the flatness surface function at coordinate (x,y), and $CT_{ref}$ is the pre-known CT number for the reference region.

In some exemplary embodiments, the correction is applied to all CT numbers where a valid surface function is available. Alternatively, the correction is applied to parts of the image where quantitative assessment of CT number is desired, e.g. ROI. Optionally, for stacks of images, correction may be applied to each image separately based on reference data for that image or may be applied to the stack of images or to a volume based on reference data from one or several images.

In some exemplary embodiments, the average value of the CT numbers actually measured in reference regions of the image may be used as parameter $CT_{ref}$ in Equation 3, e.g. in cases where the CT number of reference areas is not pre-known. Optionally, the average value of the CT numbers in reference areas in particular parts of the image, e.g. near the image center, may be used as $CT_{ref}$ in Equation 3 to determined $CT_{corr}(x,y)$. In some exemplary embodiments, image data is corrected for flatness but not calibrated relative to absolute CT number, e.g. in cases where the CT number of reference areas is not pre-known.

In some exemplary embodiments, if it is determined that the image is sufficiently flat, a global shift factor is determined (block 310) and the image data, e.g. the CT numbers are calibrated based on the determined shift factor (block 312). Typically, the global shift factor is a difference between CT numbers in a reference region after flattening and a known CT number for that reference region. In some exemplary embodiments, the shift factor is determined by comparing measured CT numbers in the identified reference regions to pre-known CT numbers associated with the reference regions. Optionally, the shift factor is determined based on a phantom with known CT number that is scanned together with the patient.

In some exemplary embodiments, correction is applied over the entire image or over ROI using the following formula:

$$CT_{corr}(x,y) = CT_{meas}(x,y) \times (1000 + CT_{ref})/(1000 + CT_{actual}) \quad \text{(Equation 4)}$$

Where $CT_{meas}(x,y)$ is the measured CT number at coordinate (x,y), $CT_{actual}$ is the CT number actually measured over reference region, and $CT_{ref}$ is the pre-known CT number for that reference region. Typically, a linear shift of CT numbers is assumed where the CT number for air is taken to be −1000. It will be appreciated that other calibration formulas can be used under different assumptions.

Although most of the embodiments of the present invention have been described in reference to identification of reference regions including a single reference tissue and/or a single pre-known CT number, it is appreciated that a plurality of regions associated with different pre-known CT numbers can be used as reference regions. In some exemplary embodiments, when a single reference tissue is not sufficiently dispersed over an image, reference regions with different pre-known CT numbers are used. In some exemplary embodiments, when reference regions are defined that include two different reference tissues, e.g. tissue1 and tissue2, measured CT numbers data in reference region of tissue2 may be calibrated to CT numbers of tissue1 by multiplying CT numbers of tissue 2 by $(1000 + CT_{ref1})/(1000 + CT_{ref2})$, where $CT_{ref1}$ and $CT_{ref2}$ are pre-known CT numbers of tissue1 and tissue2, respectively. In scans of human patients, tissue1 and tissue2 may be for example muscle and fat or muscle and external phantom/s placed alongside the patient during the scan.

Optionally, the shift factor may be determined based on one reference region and/or a specific portion of a reference region, e.g. region 404 over the aorta may be used to calibrate the images CT numbers. Optionally, when tissue of pre-known absolute CT number is not available, a phantom composed of material with pre-known CT number may be placed in the scan field along with the scanned subject and the CT number measured for the phantom can be used for calibration.

In some exemplary embodiments, when the CT number of the reference tissue is pre-known and used as $CT_{ref}$ in Equation 3, the resulted corrected image data is flatten and calibrated so that correction in blocks 310 and 312 are not required.

Figure 5:
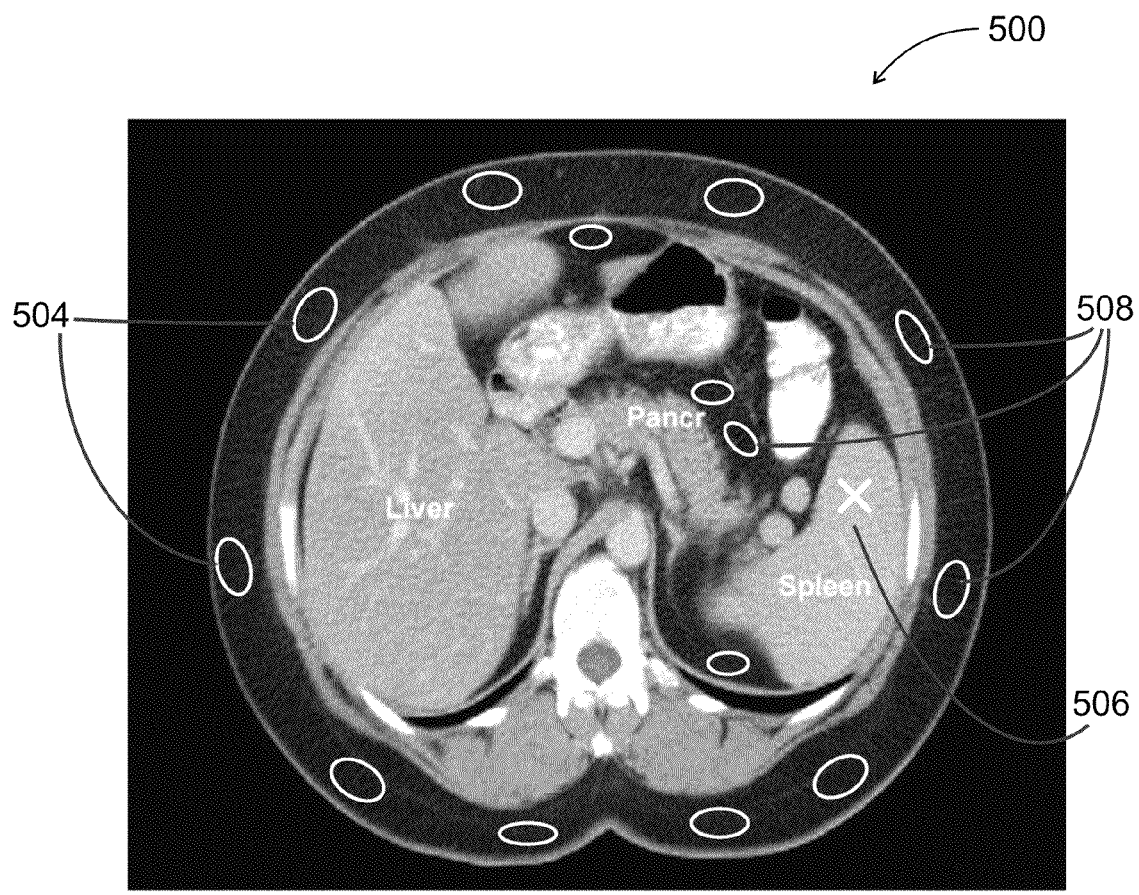
FIG. 5 showing an exemplary CT image of the abdomen from which a plurality of scattered references regions has been qualitatively identified in accordance with some embodiments of the present invention.

Reference is now made to FIG. 5 showing an exemplary CT image of the abdomen from which a plurality of scattered references regions have been qualitatively identified in accordance with some embodiments of the present invention. Image 500 shows a CT image of the abdomen with an entire body cross section within a scan FOV in which fourteen exemplary reference regions identified fat tissue. Ten reference regions 504 are subcutaneous fat regions and four reference regions 508 are isolated fat tissue regions in the inner part of the image. Alternatively, area of reference regions may be expanded by segmentation as described herein above. In some exemplary embodiments, if qualitative analysis is required for an organ 506 (marked with an FIG. 5 with an X), correction is based on measured CT numbers in specific reference regions surrounding organ 506, e.g. reference regions 504' and 508'.

Figure 6:
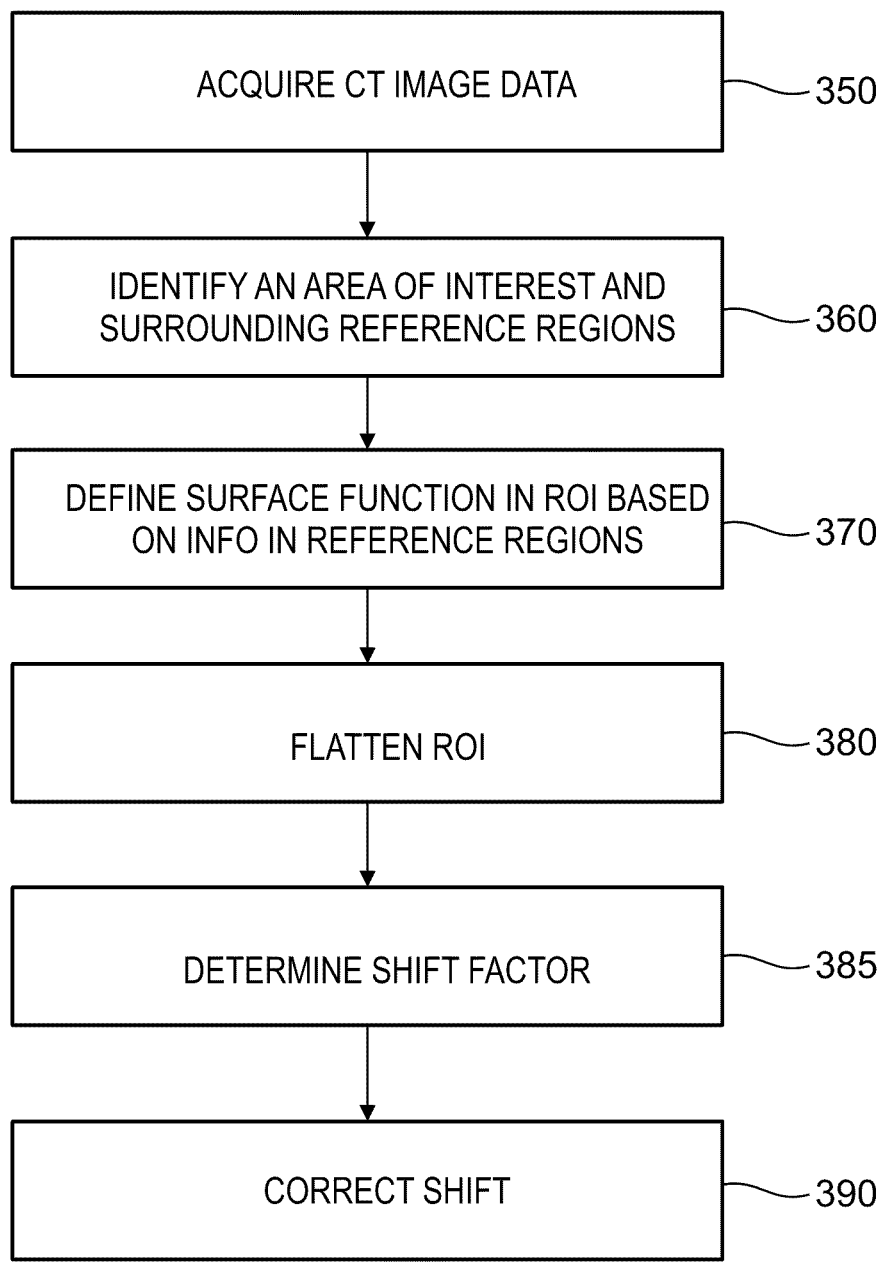
FIG. 6 is a simplified flow chart of an exemplary method for calibrating CT numbers in selected portions of a CT image using locally defined surface functions in accordance with some embodiments of the present invention.

Reference is now made to FIG. 6 showing a simplified flow chart of an exemplary method for calibrating CT numbers in selected portions of a CT image using locally defined surface functions in accordance with some embodiments of the present invention. According to some embodiments of the present invention CT image data is acquired (block 350) and one or more ROI as well as a plurality of reference regions are identified by qualitative analysis of the image data (block 360). According to some embodiments of the present invention, CT numbers in a specified ROI, e.g. organ 506 is flattened based on measured CT numbers in surrounding reference regions. In some exemplary embodiments, at least three reference regions that surround the ROI are used to flatten CT numbers in the ROI. Optionally, at least one of the reference regions used is closer to a center of rotation of the scanner than the ROI to be corrected.

According to some embodiments of the present invention, a surface shape is defined based on measured CT numbers in the reference regions and interpolating CT numbers between the reference regions (block 370). Optionally, when a ROI is not surrounded by reference regions, a surface shape is approximated by extrapolations based on a plurality of proximal reference regions. It is appreciated that other method for determining a surface function may be known which can be applied to determine spatial variation of artifacts between reference regions. According to some embodiments of the present invention, once the shape of the surface is defined, correction can be applied, e.g. based on Equation 3 (block 380). Optionally when required, a shift factor over the entire ROI can be determined (block 385), e.g. by methods described herein and the shift can be corrected to obtain calibrated CT numbers (block 390). Optionally, the shift factor is corrected for during flattening.

Figure 7:
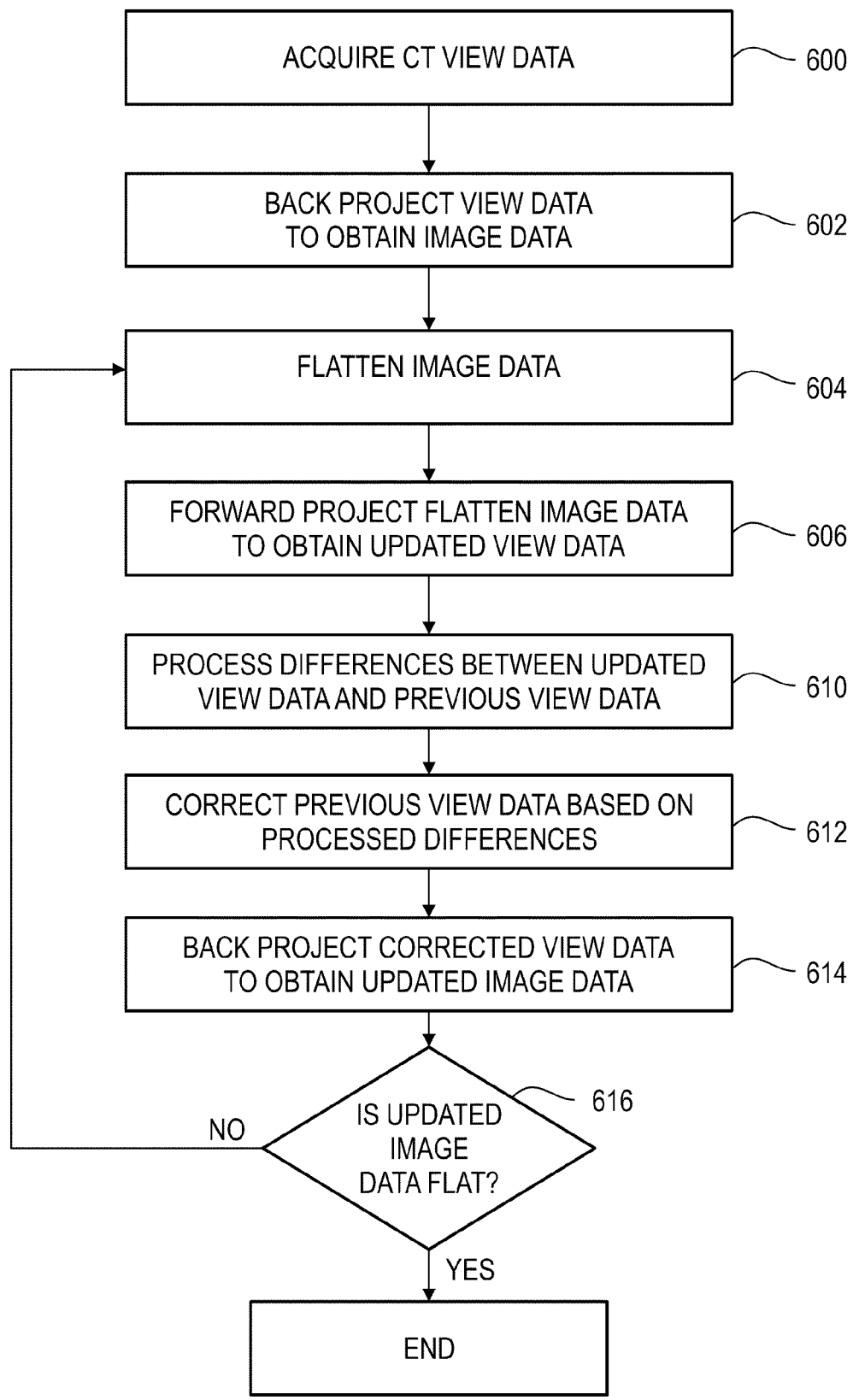
FIG. 7 is a simplified flow chart of an exemplary method for further processing flattened images in view data representation in accordance with some embodiments of the present invention.

Reference is now made to FIG. 7 showing a simplified flow chart of an exemplary method for processing flattened images using view data representation of the flattened images in accordance with some embodiments of the present invention. Typically, during CT scanning, CT view data is acquired (block 600) and back projected to obtain image data (block 602). Optionally, view data is filtered, e.g. convolved with a filter function prior back projection. According to some embodiments of the present invention, image data is flattened to reduce artifacts causing spatially variations of the CT numbers of the image (block 604). Optionally, the image data is normalized to a known CT number to compensate for artifacts causing a global shift in the CT numbers. Optionally, flattening and normalizing of image data is performed by methods described herein above.

According to some embodiments of the present invention, after flattening the image data, image data is forward projected to generate calculated view data from the flattened image (block 606). Optionally, methods for forward projection are similar to those described in incorporated U.S. Pat. No. 5,008,822. According to some embodiments of the present invention, the calculated view data is processed to further reduce artifacts and to smooth the view data. Optionally, the calculated view data (from flattened image) is subtracted from the sampled view data (previous view data) and the difference is processed and/or smoothed (block 610). Optionally, processing includes multiplying the differences by a factor less than one. According to some embodiments of the present invention, the processes differences are used to correct sampled view data (block 612). Optionally, the processed differences are subtracted from the sampled view data.

Typically, the corrected view data is then back projected to construct updated image data (block 614). Optionally, the updated image data is reassessed for flatness and the process is repeated if it is determined that the image is not sufficiently flat, e.g. sufficiently flat for a specified application (block 616). Optionally, blocks 604-614 are repeated over a plurality of iterations until differences between the previous view data and the back projected view data are below a defined threshold. In some exemplary embodiments, the number of iterations or the maximum number of allowed iterations is predefined. Optionally, during iterations the new calculated view data is compared to and corrected against previously calculated view data. Optionally, image data is calibrated to correct for a global shift in CT numbers, e.g. using known CT numbers at the end of the iterations process.

Figure 8:
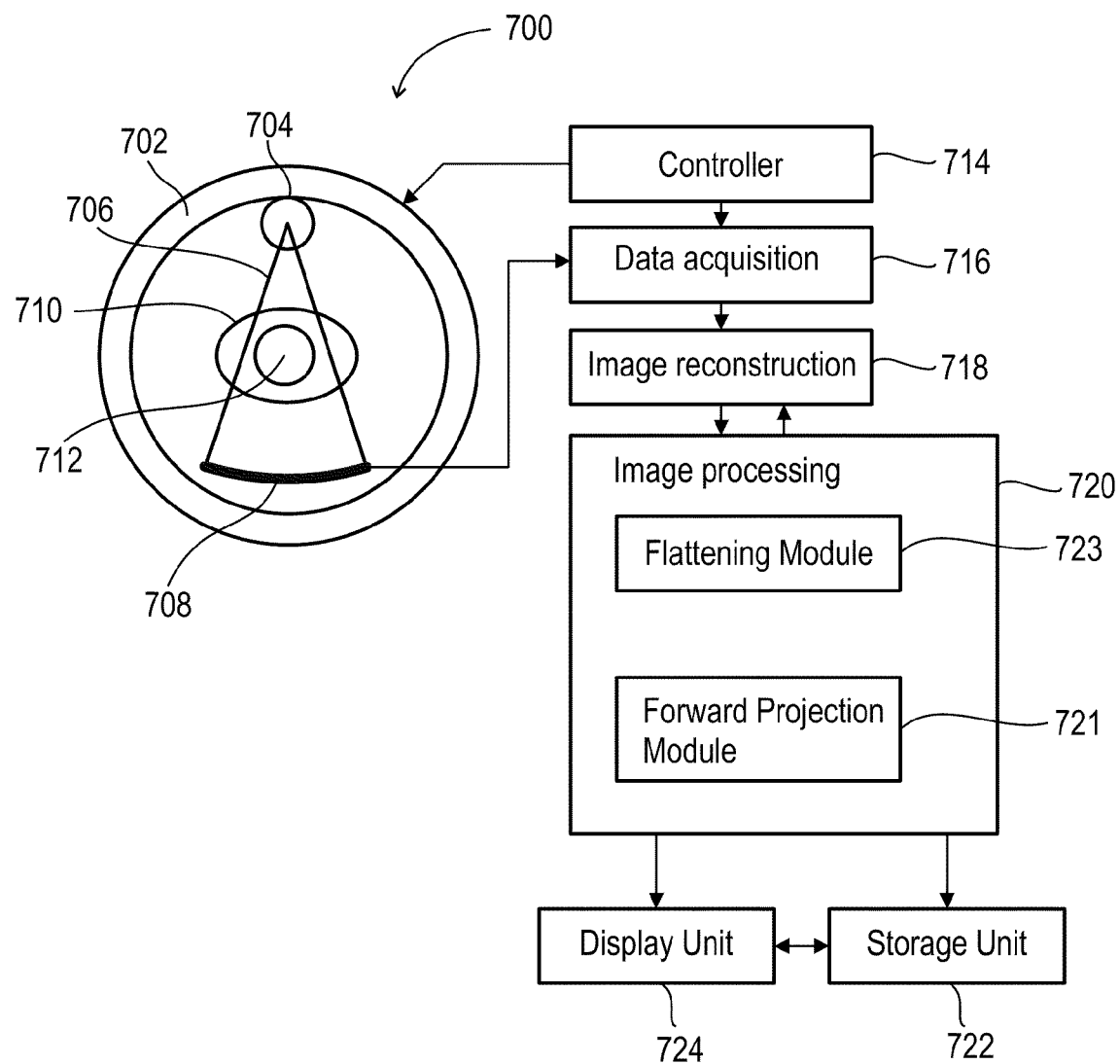
FIG. 8 is a simplified block diagram of a CT system in accordance with some embodiments of the present invention.

Reference is now made to FIG. 8 a simplified block diagram of a CT system in accordance with some embodiments of the present invention. Exemplary CT system 700 includes a gantry 702 carrying an X-ray source 704, emitting radiation beam 706. Detector 708 is typically disposed opposite source 704 and receives radiation 706. A subject 710, e.g. a patient is positioned between radiation source 704 and detector 708 and attenuates radiation from source 704 received by detector 708. In some cases radiation beam 706 is defined to cover the entire cross section of scanned subject 710. In other cases beam 706 is defined to cover a volume of interest 712 within scanned subject 710, as shown in FIG. 8. The volume of interest may be the heart within the chest, the spine or other organs in a patient's body. Typically, a controller 714 is operative to rotate the source 704 and detector 708 during scanning, activate the X-ray radiation and monitor other functions of the CT scanner. Data acquisition circuitry 716 acquires view data from detector 708 during the scan and an image reconstruction unit typically back projects the view data to construct image data. Typically image data is processed with image processing unit 720.

In some exemplary embodiments of the present invention, constructed image data obtained from image reconstruction unit 718 are assessed for flatness with flattening module 723. Optionally, an image display unit 724 displays the constructed image data and image processing unit 720 assesses flatness based on user input. According to some embodiments of the present invention, flattening module 723 is operable to flatten image data using methods described herein above. Optionally, flattening is a user assisted process in which image processing unit receives input from the user based on displayed image data. In some exemplary embodiments, image processing unit includes a forward projecting module 721 for constructing view data from received image data. Optionally, forward projecting module 721 is integrated with image reconstructing unit 718. Optionally, constructed view data is further processed by images processing unit 720 and subsequently forwarded to image reconstruction unit 718 for reconstruction. Typically, storage unit 722 stores image data, view data and pre-defined parameters required for assessing and processing the image data.

It will be appreciated that system 700 typically includes additional parts which are not shown for clarity. Although system 700 is analogous to a third generation rotate-rotate CT scanner, the methods and system described herein can also be applied to a fourth generation CT, electron beam CT, single or multi-slice CT, a volumetric cone beam CT and the like.

It will be also appreciated that system 700 is shown as an integrated systems but elements such as 718, 720, 721, 722, 723, 724 and/or their functionality may be implemented as a separate system and operated on data acquired by CT scanner 700 independently of the scanner.

It is noted that each of elements 714, 716, 718, 720, 721, 722, 723 and/or their functionality may be implemented by hardware, by software or by firmware or by a combination thereof using an operating system.

It is also noted that although embodiments of the present invention have been mostly described in reference to CT scanning and correction of CT numbers for human tissue, the methods and systems described herein can also be applied for CT scanning of other subject matter.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

What is claimed is:

1. A method of correcting CT numbers in image data, the method comprising:
selecting at least one reference region in a CT image of an object, wherein the at least one reference region is a portion of the object associated with substantially same CT number when no artifacts are present in the CT image;
estimating artifacts in at least one other region in the same CT image based at least in part on detected CT numbers in the at least one reference region, wherein the at least one other region is another portion of the same object; and
correcting CT numbers in the at least one other region in the CT image based on the estimated artifacts.

2. The method according to claim 1 wherein the selecting includes selecting a plurality of reference regions dispersed across the CT image, the plurality of reference regions are within the object.

3. The method according to claim 1, further comprising segmenting image parts including the substantially same CT number.

4. The method according to claim 1, wherein the at least one reference region is a region associated with a pre-known CT number.

5. The method according to claim 4, further comprising calibrating the CT numbers based on a difference between the pre-known CT number and an average CT number in the at least one reference region.

6. The method according to claim 1, wherein the at least one reference region is a region of muscle tissue, fat, blood, or brain tissue of a patient being imaged.

7. The method according to claim 1, wherein selecting the at least one reference region is performed by computer assisted selection.

8. The method according to claim 1, wherein a CT number for the at least one reference region is determined from an average of pixel values over a defined area in the at least one reference region.

9. The method according to claim 1, further comprising defining a surface shape function of the at least one other region from detected CT numbers in the at least one reference region.

10. The method according to claim 1, wherein estimating artifacts in the at least one other region is based on interpolation of CT number gradients determined from the at least one reference region.

11. The method according to claim 1, wherein the CT image is one of a stack of images, and wherein the correcting is performed on the stack of images based estimating artifacts on one or more images of the stack.

12. The method according to claim 1, wherein the CT image includes a volumetric image and wherein selecting at least one reference regions includes selecting a volumetric regions.

13. The method according to claim 1, further comprising assessing the flatness of a portion of the CT image based on detected CT numbers in the at least one reference region.

14. The method according to claim 1, comprising selecting at least two reference regions associated with a different pre-known CT number.

15. The method according to claim 1, wherein the at least one other region is a region of interest from which a quantitative analysis is performed.

16. The method according to claim 1, further comprising:
forward projecting the calibrated image data;
processing the forward projected data; and
back projecting the forward projected data.

17. A scanning system providing corrected CT image data comprising:
a data acquisition unit for acquiring view data from a detector in a CT scanner for imaging an object;
an image reconstruction unit for reconstructing image data from the view data to obtain a CT image;
and an image processing unit for calibrating image data reconstructed from the image reconstruction unit, wherein the image processing unit is operative to analyze CT numbers in at least one selected reference region in the CT image and to estimate artifacts in the at least one other region of the same CT image at least partially based on analysis of the CT numbers in the at least one selected reference region, wherein both the at least one selected reference region and the at least one other region are portions of the same object being imaged and wherein the at least one selected reference region is a region associated with a substantially same CT number when no artifacts are present in the CT image.

18. The system according to claim 17, wherein the image processing unit is operative to select the reference regions.

19. The system according to claim 17, wherein the image processing unit is operative to select regions associated with pre-known CT numbers.

20. The system according to claim 19, wherein the image processing unit is operative to select regions of at least one of muscle tissue, fat, blood, and brain tissue of a patient.

21. The system according to claim 17, wherein the image processing unit is operative to segment image parts known to include a substantially same CT number.

22. The system according to claim 17, wherein the image processing unit is operative to define a shape function for the at least one other region of the CT image based on detected CT numbers in the at least one reference region.

23. The system according to claim 17, wherein the image processing unit is operative to estimate artifacts in the at least one other region based on interpolation of CT number gradients determined from the at least one reference region.

24. The system according to claim 17, wherein the CT image is a volumetric image and wherein the image processing unit is operative to analyze CT numbers in at least one selected volumetric reference region, wherein the volumetric region is from a portion of the volumetric image that represents the object.

25. The system according to claim 17, wherein the CT image is one of a stack of CT images, and wherein the image processing unit calibrates the stack of images based estimating artifacts on one or more images of the stack.

26. The system according to claim 17, wherein the image processing unit is operative to assess a flatness of a portion of the CT image based on detected CT numbers in the at least one reference region.

27. The system according to claim 17, wherein the image processing unit is operative to perform quantitative analysis on the at least one other region, wherein the quantitative analysis includes one of coronary artery calcium testing, bone mineral density evaluation, fat content of tissue evaluation, iron build up in liver evaluation, and contrast agent perfusion determination.

28. The system according to claim 17, wherein the image processing unit is operative to forward projecting calibrated image data, processing the forward projected data.

29. A method of correcting CT numbers in image data, the method comprising:
- selecting at least one reference region in a CT image of a patient, wherein the selected region is tissue with a known CT number, wherein the tissue is the patient's tissue;
- estimating artifacts in at least one other region of the same CT image based on comparing detected CT numbers in the at least one reference region and known CT numbers for that region, wherein the at least one other region is within the patient; and
- correcting CT numbers in the at least one other region of the CT image based on the estimated artifacts.

30. The method according to claim 29, wherein the detected CT numbers are average CT numbers over a sample area of the reference region.

31. The method according to claim 29, wherein the at least two reference regions are regions of muscle tissue, fat, blood, or brain tissue of the patient.

32. The method according to claim 29, wherein the CT image is one of a stack of images, and wherein the correction is performed on the stack of images based estimating artifacts on one or more images of the stack.

33. The method according to claim 29, wherein the CT image includes a volumetric image and wherein selecting at least one reference region includes selecting a volumetric region.

34. The method according to claim 29, wherein the at least one reference region includes at least two regions associated with a different pre-known CT number.

35. The method according to claim 29, wherein the at least one other region is a region of interest from which a quantitative analysis is performed.

36. The method of claim 1 wherein the object being imaged is a patient.

37. The system of claim 17, wherein the object being imaged is a patient.

38. A method of correcting CT numbers in image data, the method comprising:
- selecting at least one reference region in at least one CT image of an object, wherein the CT image is from a CT image stack and wherein the selected region is associated with substantially same CT number when no artifacts are present in the CT image, wherein the at least one reference region is a portion of the imaged object;
- estimating artifacts in at least one other region in the CT image stack based at least in part on detected CT numbers in the at least one reference region, wherein the at least one other region is another portion of the same imaged object; and
- correcting CT numbers in the at least one other region based on the estimated artifacts.

* * * * *